Figure 1:
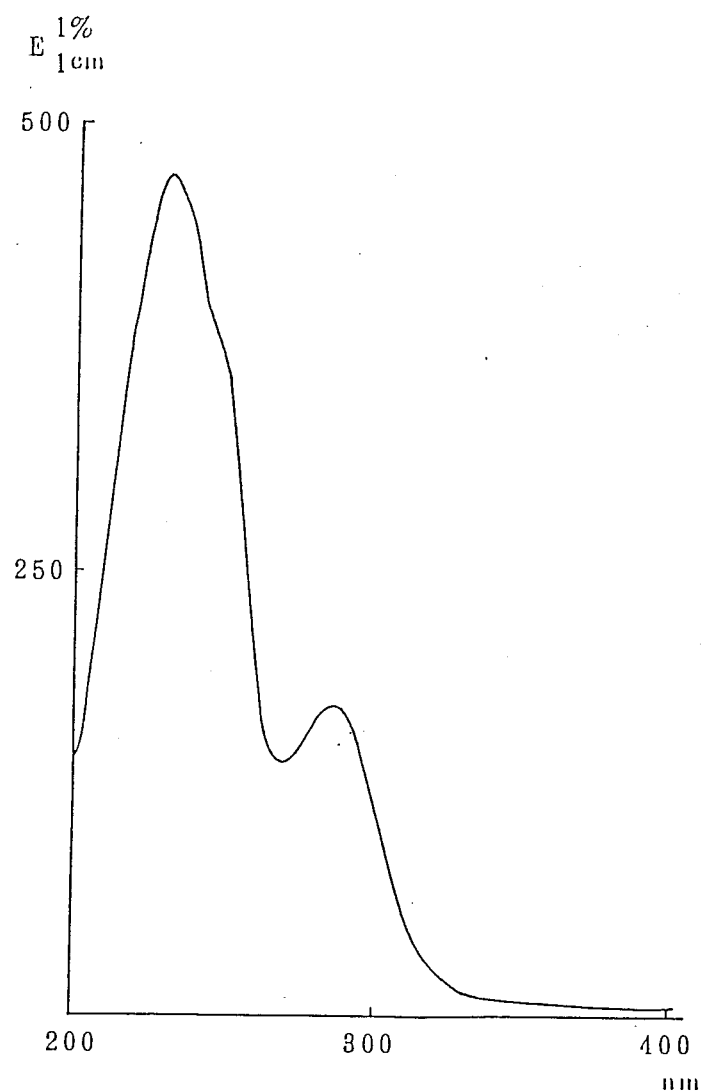

United States Patent [19]

Kumagai et al.

[11] Patent Number: 4,764,602

[45] Date of Patent: Aug. 16, 1988

[54] ANTIBIOTICS, AND THEIR PRODUCTION

[75] Inventors: Kazuo Kumagai, Toyonaka; Kiyoshi Taya, Nishinomiya; Shin Tanaka, Ibaraki; Koichi Moriguchi, Otsu; Masatomo Fukasawa, Nishinomiya; Akio Fukui, Ashiya, all of Japan

[73] Assignees: Sumitomo Chemical Company; Sumitomo Pharmaceuticals Company, Limited, both of Osaka, Japan

[21] Appl. No.: 943,906

[22] Filed: Dec. 19, 1986

[51] Int. Cl.⁴ .......................................... C07H 17/08
[52] U.S. Cl. .................................................. 536/7.1
[58] Field of Search ....................................... 536/7.1

[56] References Cited

PUBLICATIONS

Description of Lecture at General Meeting of the Agricultural Chemical Society of Japan, 3/10/86 (Japanese & English translation).

Primary Examiner—J. R. Brown
Assistant Examiner—Elli Peselev
Attorney, Agent, or Firm—Birch, Stewart, Kolasch & Birch

[57] ABSTRACT

A novel antibiotic of the formula:

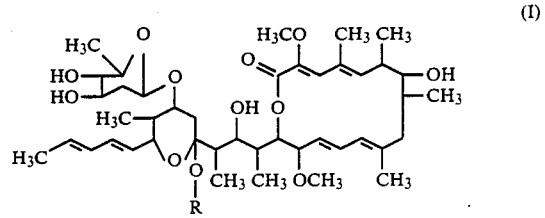

wherein R is a hydrogen atom or a methyl group and preparation of the antibiotic by cultivating Nocardia sp. SC-4710.

9 Claims, 5 Drawing Sheets

ANTIBIOTICS, AND THEIR PRODUCTION

The present invention relates to antibiotics and their production. More particularly, it relates to novel antibiotics designated "PC-766B" and "PC-766B'" and antibiotic substances comprising at least one of them, and their production.

In the course of search for new antibiotics, it has been found that a Nocardia species indexed SC-4710 in the collection in the Research Laboratory of Sumitomo Chemical Company, Limited, Osaka, Japan, and on deposit with the Fermentation Research Institute, Agency of Industrial Science and Technology, Ibaraki-ken, Japan under the deposition number FERM P-8233 produces antibiotics. When grown in a suitable nutrient medium, at least two different antibiotics which are representable by the following formula are produced:

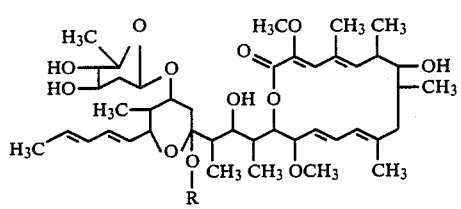

(I)

wherein R is a hydrogen atom or a methyl group. When R is a hydrogen atom, the antibiotic (I) is called "PC-766B". When R is a methyl group, the antibiotic (I) is called "PC-766B'".

Nocardia sp. SC-4710 has been isolated from a soil sample collected at Shiga-ken, Japan and shows the following microbiological properties:

(1) Morphological characteristics:

On a agar medium and in a liquid medium, the substrate mycelium elongates well and branches, and it is sometimes divided into bacillus-like or branched short rods. Good growth is observed on various media for classification. On the substrate mycelium, white to grayish white aerial mycelia are formed. Aerial mycelia are lightly wavy or spiral and irregularly branched. On observation of the grown culture by a scanning electron microscope, 3 to 10 spores in a chain are seen on the aerial mycelium; the shape of spore is ellipsoidal, the size is from $0.3 \times 0.8$ micron to $0.4 \times 1.0$ micron and the surface is smooth; any peculiar structure such as sporangium and sclerotium is not ovserved.

(2) Cultural characteristics:

According to the Sharing and Gottlieb's method [International Journal of Systematic Bacteriology, Vol. 16, page 313 (1966)], the culture media were prepared, and the test was carried out. Observation was made after incubation for a period of three weeks at 27° C. The results are shown in Table 1 wherein the colors were determined in comparison with the standard colors in "Color Tone Mannual" edited by Japan Color Research Laboratory.

TABLE 1

| Medium | Growth of aerial mycelium | Growth of substrate mycelium | Production of soluble pigment |
|---|---|---|---|
| Yeast extract-malt extract agar (ISP 2) | Good (pinkish white) | Good (yellowish brown) | None |
| Oat meal agar (ISP 3) | Poor (grayish white) | Poor (pale reddish yellow) | None |
| Inorganic salts starch agar (ISP 4) | Poor (pinkish white) | Poor (dull reddish yellow) | None |
| Glycerol-asparagine agar (ISP 5) | Moderate (brownish white) | Moderate (dull reddish yellow) | None |
| Peptone-yeast extract-iron agar (ISP 6) | None | Poor (dull reddish yellow) | None |
| Tyrosine agar (ISP 7) | Moderate (yellowish white) | Moderate (grayish yellow) | None |
| Sucrose-nitrate agar | Poor (grayish white) | Poor (grayish yellow) | None |
| Glucose-asparagine agar | Moderate (pale beige) | Good (dull yellow) | None |
| Nutrient agar | Poor (pale beige) | Poor (dull yellow) | None |
| Bennet agar | Good (white) | Moderate (dull yellowish orange) | None |

(3) Physiological characteristics:

Observation was made according to the standard method. The results are shown in Table 2.

TABLE 2

| Test | Result |
|---|---|
| Growth temperature | 17 to 37° C. |
| Optimum temperature for growth | 22 to 32° C. |
| Gelatin liquefaction | Negative |
| Starch hydrolysis | Negative |
| Nitrate reduction | Positive |
| Hydrogen sulfide production | Slightly positive |
| Milk peptonization | Slightly positive |
| Milk coagulation | Slightly positive |
| Melanin-like pigment production | Negative |

(4) Utilization of carbon sources

The utilization of carbon sources on the Pridham-Gottlieb agar medium is shown in Table 3 wherein the marks "+" and "++" indicate respectively good and better utilization and the mark "−" indicates no utilization.

| Carbon source | Result |
|---|---|
| None | − |
| L-Arabinose | − |
| D-Xylose | − |

-continued

| Carbon source | Result |
| --- | --- |
| D-Glucose | ++ |
| D-Fructose | ++ |
| Sucrose | − |
| Inositol | ++ |
| L-Rhamnose | − |
| Rhaffinose | − |
| D-Mannitol | + |

(5) Bacterial composition:

Diaminopimelic acid in the bacterial cell is the meso form, and arabinose and galactose were detected as the saccharides. By the analysis of the phopholipids according to the Lechevalier's method [Biochemical Systematics and Ecology, Vol. 5, page 249 (1977)], phosphatidylinositol, phosphatidylinositol dimannoside, diphosphatidylglycerol and phosphatidylethanolamine were detected, but phosphatidylcholine was not detected. On the analysis of micolic acid according to the Lechevalier's method [Canadian Journal of Microbiology, Vol. 19, page 965 (1973)] and the Minikin's [Journal of Chromatography, Vol. 188, page 221 (1980)], the spot of nocardomicolic acid methyl ester was detected.

From the above observation results, the characteristics of the microorganism SC-4710 are summarized as follows: the cell wall type is Type IV, and the phospholipid type is Type PII. As the cultural properties, the substratum mycelium shows brown to pale yellow, and the aerial mycelium shows white to grayish white. Morphologically, spores are formed in chain on the aerial mycelium, and their surfaces are smooth. Based on these characteristics, the microorganism SC-4710 has been classified to Nocardia and named Nocardia sp. SC-4710 (FERM P-8233; corresponding to FERM BP-1203 as the International Deposition Number under the Budapest Treaty).

According to this invention, the antibiotics (I) of the invention can be produced during cultivation of a standard strain of Nocardia sp. SC-4710 or its natural or artificial variant or mutant in an aqueous nutrient medium. The composition of this nutrient medium may be varied over a very wide range. Essentially what is required is a carbon source, a nitrogen source and trace inorganic elements. Examples of suitable carbon sources are glucose, maltose, starch, dextrin, glycerol, molasses, etc. Examples of suitable nitrogen sources are soybean meal, corn steep liquor, cotton seed flour, peptone, meat extract, yeast extract, casein hydrolyzate, ammonium salts, nitrates, etc. Examples of suitable sources of inorganic elements are mineral salts such as chlorides, carbonates and phosphates of magnesium, potassium, calcium, sodium, iron, manganese, etc.

Cultivation is usually carried out under aerobic conditions, especially under aeration and agitation. The temperature for cultivation may be appropriately decided within a range where the microorganism grows and the antibiotics (I) are produced. A preferred temperature range is from about 25° to 30° C. The pH is normally from about 7 to 8. Within a cultivation period of about 80 to 120 hours, the antibiotic potency accumulated in the nutrient medium reaches usually the highest.

For recovery of the antibiotics (I) from the fermentation broth after the cultivation, there may be adopted any conventional procedure as adopted for separation of any antibiotic from a fermentation broth comprising the same. For instance, the procedure utilizing the difference in solubility between the objective substance and impurities, the procedure utilizing the difference in adsorption affinity onto various adsorbents such as activated carbon, macroporous non-ionic resins, silica gel and alumina, the procedure using ion exchange resins for removal of impurities, etc. may be adopted alone or in combination.

A typical example for separation and purification of the antibiotics (I) from the fermentation broth after cultivation is as follows:

The fermentation broth is separated into the bacterial body and the supernatant or filtrate by centrifugation or filtration. The bacterial body is extracted with acetone or methanol. The extract is then extracted with a suitable organic solvent for the antibiotics (I) such as ethyl acetate or n-butanol. On the other hand, the supernatant or filtrate is extracted with an organic solvent which is not miscible with water and can dissolve the antibiotics (I) therein such as ethyl acetate, n-butanol or methylisobutylketone. The organic solvent extracts comprising the antibiotics (I) are combined together, and a per se conventional procedure for purification of a fat-soluble substance is applied thereto to recover the antibiotics (I). For instance, the ethyl acetate extract is washed with water and concentrated under reduced pressure, followed by addition of n-hexane or the like to precipitate the active component. The precipitate is collected by centrifugation or filtration to obtain the crude product comprising the antibiotics (I).

For purification, the above crude product is subjected to column chromatography using a carrier having a molecular sieve effect such as Sephadex LH-20 (manufactured by Pharmacia, Sweden) and a developing solvent such as alcohols (e.g. methanol), halogenated hydrocarbons (e.g. chloroform), and their mixtures. For further purification, the resulting product may be subjected to adsorptive chromatography using such an adsorbent as a carrier generally used for adsorptive separation of antibiotics (e.g. adsorptive resins, silica gel, alumina). When silica gel is used as the adsorbent, chromatographic separation may be effected changing the mixing proportion of a polar solvent such as alkanols (e.g. methanol) and a non-polar solvent such as halogenated alkanes (e.g. chloroform).

In order to isolate PC-766B and PC-766B' from the above purified product, chromatography using said adsorbent may be applied repeatedly thereto. When, for instance, silica gel is used as the adsorbent, the silica gel on which the antibiotics (I) are adsorbed may be developed with a solvent system consisting of benzene and ethyl acetate, whereby PC-766B' and PC-766B are eluted in this order. After assaying the purity by TLC (thin layer chromatography) or HPLC (high performance liquid chromatography), the eluted fractions are concentrated under reduced pressure to dryness so that PC-766B and PC-766B' are respectively obtained as powdery crystals.

PC-766B and PC-766B' can be both manufactured by cultivation of Nocardia sp. SC-4710. PC-766B' may be also manufactured by methylation of PC-766B under appropriate conditions. This methylation can be effected, for instance, by keeping a solution of PC-766B in methanol at room temperature (e.g. 20° to 25° C.).

The chemical structures of the antibiotics (I) were determined by spectroscopic investigation. Some characteristic physico-chemical properties of PC-766B and PC-766B' are shown below:

1. PC-766B

Figure 2:
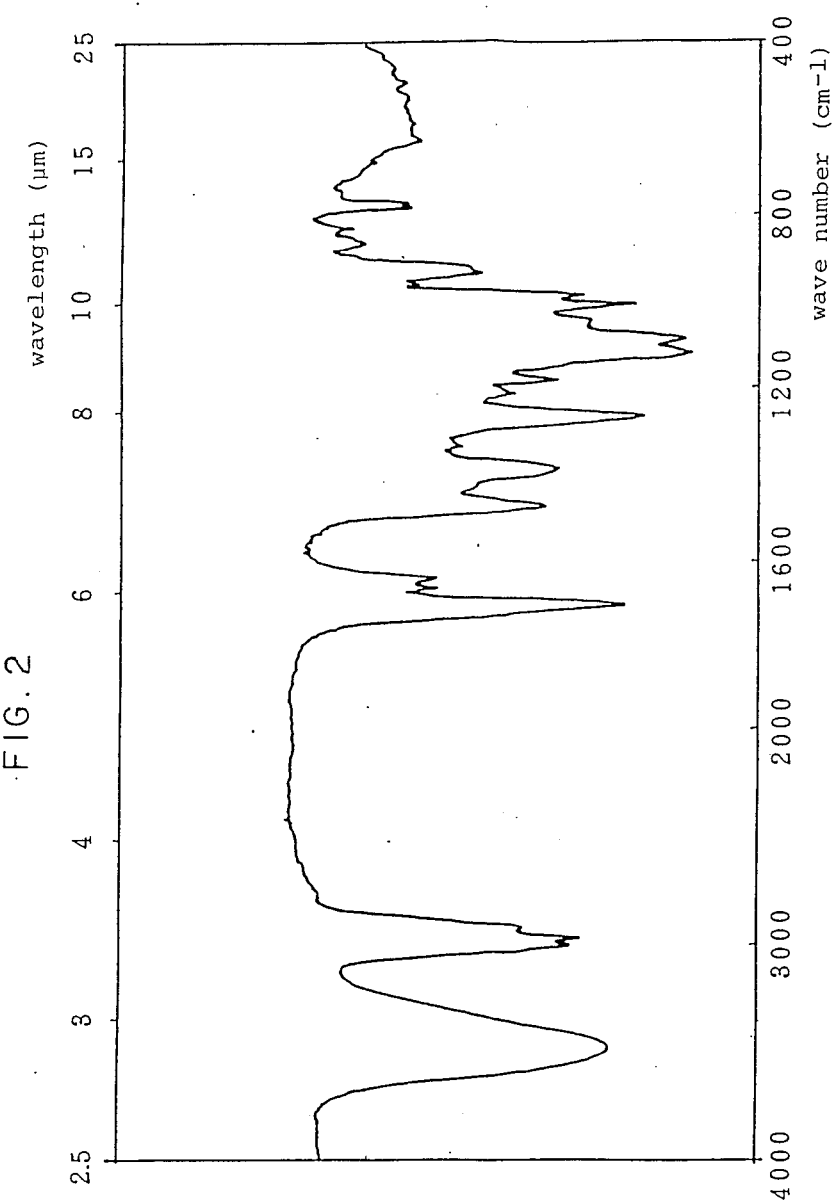
Figure 3:
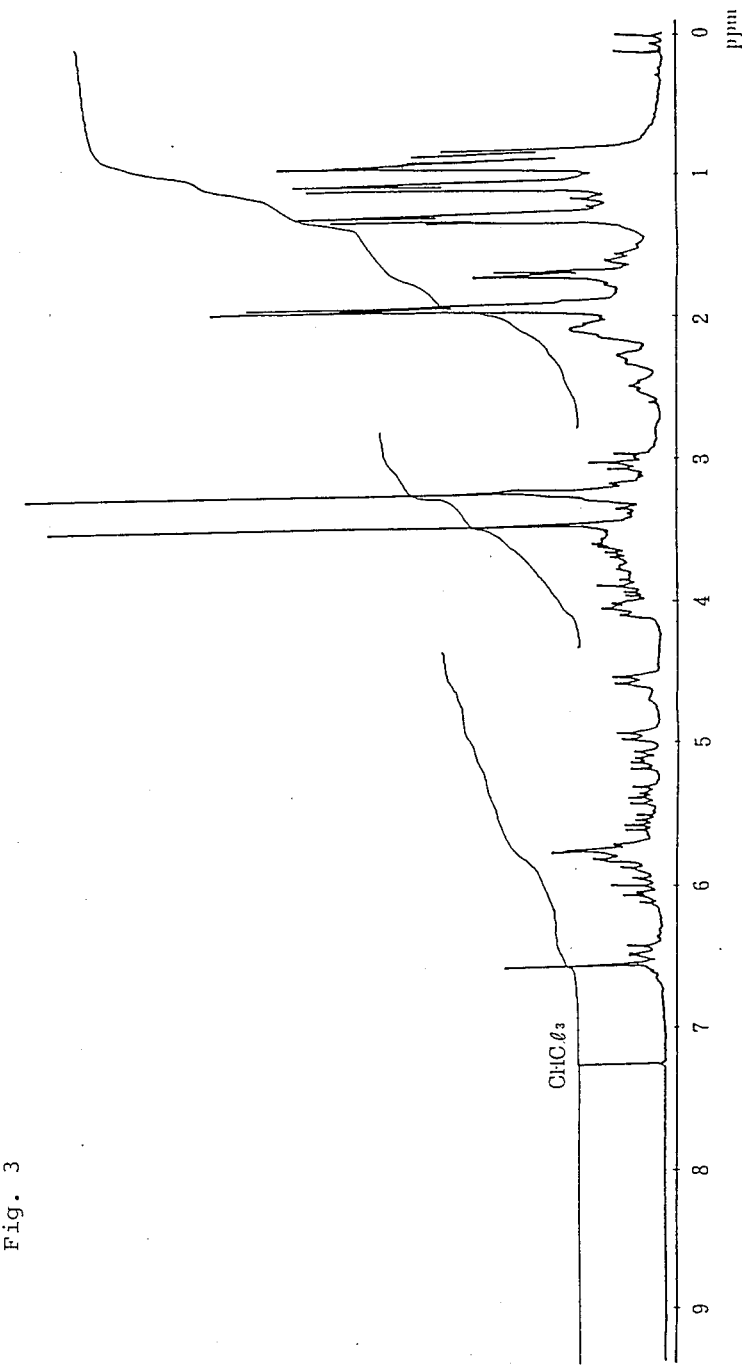
Figure 4:
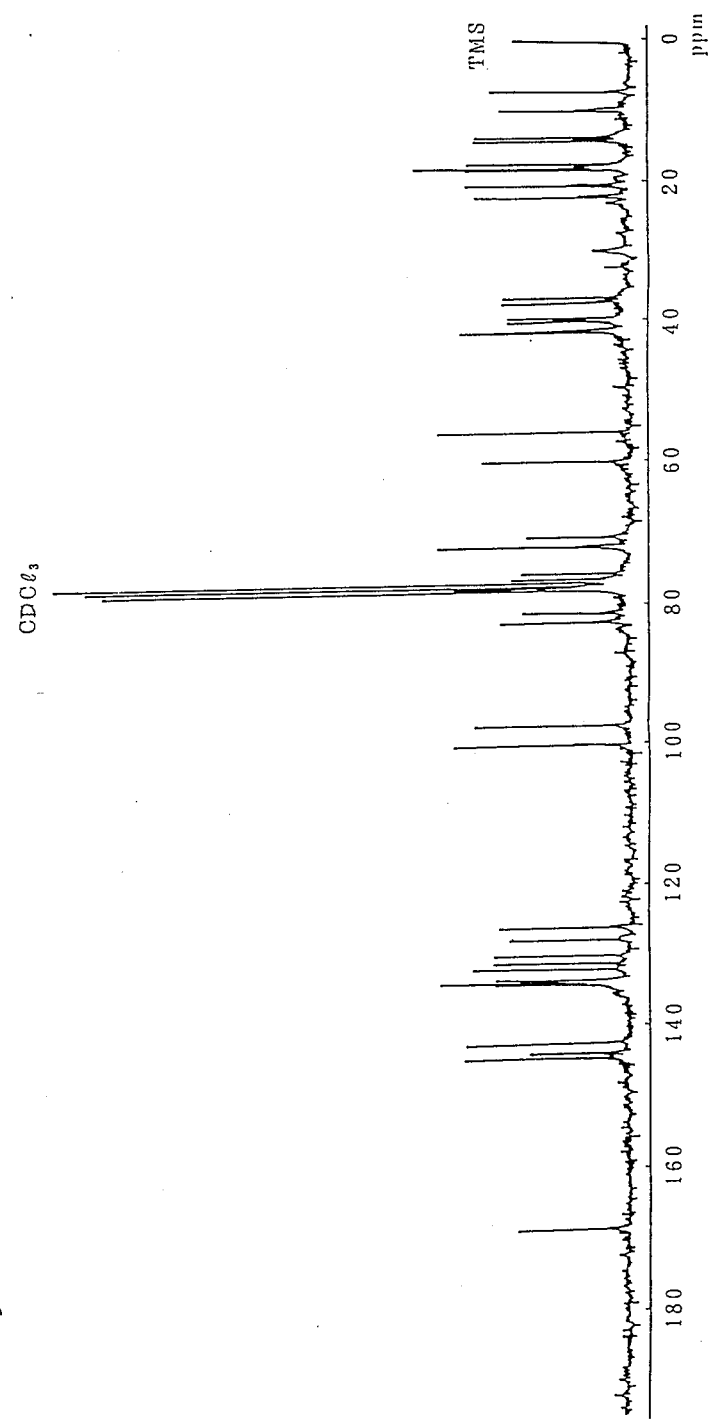

Appearance: colorless amorphous powder.
Elemental analysis: C, 61.29%; H, 8.11%.
Molecular weight: 776.
Mass spectrographic analysis: FD, FAB-MS; m/z 799 (M+ +Na), m/z 815 (M+ +K).
Molecular formula: $C_{43}H_{68}O_{12}$.
Melting point: 132°–134° C.
Specific rotation: $[\alpha]_D^{20} = +17.7°$ (C=0.61, methanol).
Solubility: soluble in methanol, chloroform and ethyl acetate; insoluble in n-hexane and water.
Color reaction: positive in $I_2$ absorption and anisaldehyde reaction; negative in ninhydrin reaction.
TLC (silica gel): chloroform-methanol (15:1 by volume), Rf=0.14; benzene-ethyl acetate (1:4 by volume), Rf=0.23.
UV absorption spectrum (in methanol): as shown in FIG. 1 of the accompanying drawings.
IR absorption spectrum (in KBr tablet): as shown in FIG. 2.
$^1$H-NMR spectrum (200 MHz, in $CDCl_3$, TMS standard): as shown in FIG. 3.
$^{13}$C-NMR spectrum (50.3 MHz, in $CDCl_3$, TMS standard): as shown in FIG. 4.

Figure 5:
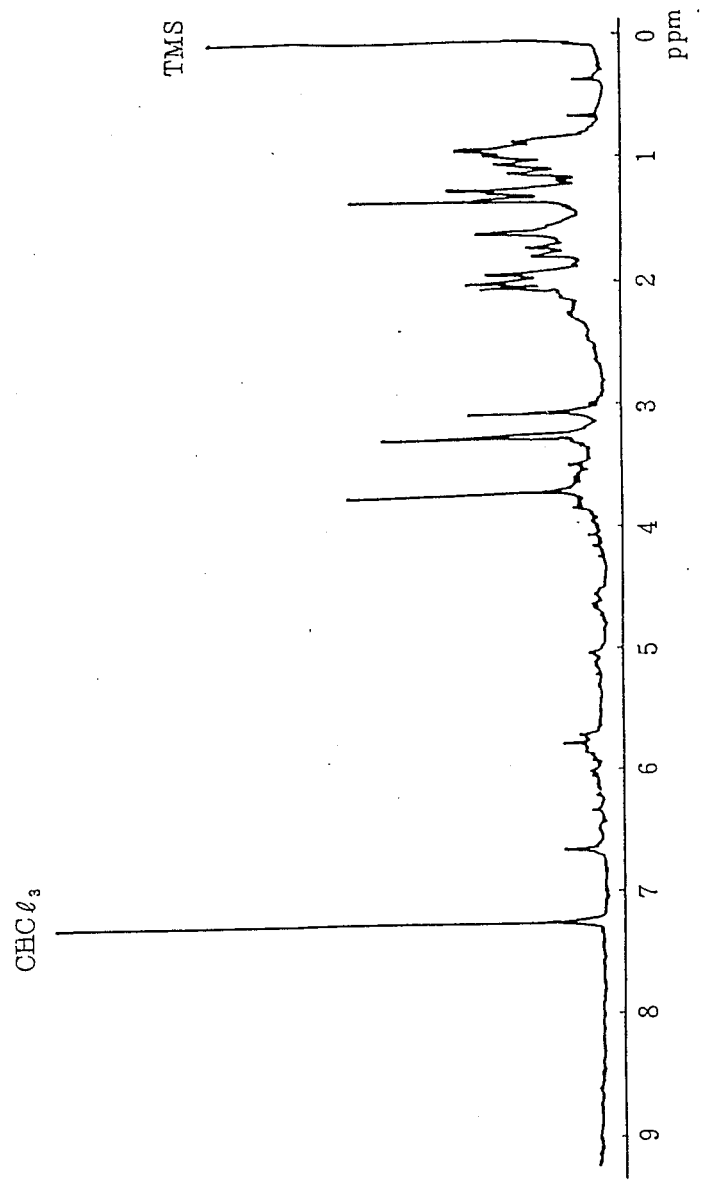

2. PC-766B'
Appearance: colorless amorphous powder.
Molecular weight: 790.
Molecular formula: $C_{44}H_{70}O_{12}$.
Solubility: soluble in methanol, chloroform and ethyl acetate; insoluble in n-hexane and water.
Color reaction: positive in $I_2$ absorption and anisaldehyde reaction; negative in ninhydrin reaction.
TLC (silica gel): chloroform-methanol (15:1 by volume), Rf=0.18; benzene-ethyl acetate (1:4 by volume), Rf=0.35.
$^1$H-NMR spectrum (90 MHz, in $CDCl_3$, TMS standard): as shown in FIG. 5.

The antibiotics (I) exhibit significant antimicrobial potency against various microorganisms. The minimum inhibitory concentrations (MIC) of PC-766B against various microorgnisms as measured by the agar dilution method are shown in Table 4. PC-766B' also shows similar antimicrobial potency.

TABLE 4

| Microorganisms | MIC (μg/ml) | Culture Medium*1 |
| --- | --- | --- |
| Staphylococcus aureus 209P | 12.5 | 1 |
| Staphylococcus epidermidis IAM 1296 | 6.25 | 1 |
| Micrococcus luteus ATCC 9341 | 1.56 | 1 |
| Streptococcus pyogenes Cook | 3.13 | 1 |
| Bacillus subtilis ATCC 6633 | 6.25 | 1 |
| Bacillus cereus IAM 1029 | 3.13 | 1 |
| Escherichia coli NIJH JC-2 | >200 | 1 |
| Klebsiella pneumoniae ATCC 10031 | >200 | 1 |
| Proteus mirabilis GN 2425 | >200 | 1 |
| Pseudomonas aeruginosa T | >200 | 1 |
| Serratia marcescens X 100 | >200 | 1 |
| Candida albicans MTU 12001 | >100 | 2 |
| Cryptococcus neoformans MTU 13001 | 12.5 | 2 |
| Trichophyton mentagrophytes MTU 19001 | >100 | 2 |
| Aspergillus fumigatus MTU 16001 | >100 | 2 |

Note: *1 1: Modified Muller-Hinton agar medium; 2: Sabouraud's agar medium.

Practical and presently preferred embodiments of this invention are illustratively shown in the following Examples wherein part(s) and % are by weight, unless otherwise indicated.

EXAMPLE 1

A loopful of Nocardia sp. SC-4710 (FERM P-8233) cultured on a slant agar was inoculated to a seed culture medium, which was then subjected to shaking culture at 27° C. for 5 days. The resulting seed culture was added to a pre-culture medium in an amount of 2% by volume, and shaking culture was carried out at 27° C. for 5 days. The resulting pre-culture was added to a nutrient medium (50 liters) charged in a 90 liter volume jar fermenter in an amount of 2% by volume, and cultivation was carried out at 27° C. for 4 days under an aeration amount of 25 liters per minute at an agitation rate of 200 r.p.m. All of the seed culture medium, the pre-culture medium and the nutrient medium comprised glucose (2.5%), soybean meal (1.5%), yeast extract (0.2%) and calcium carbonate (0.4%) and were used after adjustment to pH 7.2 and sterilization at 121° C. for 20 minutes.

EXAMPLE 2

The fermentation broth after cultivation as in Example 1 (50 liters) was centrifuged to separate it into the microbial body and the supernatant. The microbial body in a wet state was shaken with acetone (5 liters) and filtered, and this operation was repeated twice. The acetone extracts (15 liters) were combined together and concentrated under reduced pressure to make a volume of about 100 milliliters. The concentrate was shaken with a mixture of water (1 liter) and ethyl acetate (1 liter) to extract the active fraction. Separately, said supernatant was adjusted to pH 7.0 and shaken with an equal volume of ethyl acetate. The ethyl acetate extract was washed with water (30 liters), combined with the extract comprising the active fraction and concentrated under reduced pressure. To the concentrate, n-hexane was added. The precipitate was collected by filtration and dissolved in a mixture of chloroform and methanol (1:1 by volume) (100 ml). The resultant solution was placed on a column of Sephadex LH-20 (manufactured by Pharmacia) (500 ml) equilibrated with a mixture of chloroform and methanol (1:1 by volume) and eluted with a mixture of chloroform and methanol to obtain fractions, of which each had a volume of 50 milliliters. The active fractions were concentrated under reduced pressure to dryness, and the residue was dissolved in chloroform (about 50 ml). The resulting solution was added to a column of silica gel ("Kiesel Gel 60" manufactured by E. Merck in W. Germany, 63 to 200 microns) (500 ml), and the column was eluted with chloroform and then a mixture of chloroform and methanol (97:3 by volume) to collect fractions, of which each had 50 milliliters. The active fractions were concentrated under reduced pressure to dryness to give a crude product (640 mg) of the antibiotic substance "PC-766" comprising PC-766B as the major product with a trace amount of PC-766B'.

EXAMPLE 3

The crude product of the antibiotic substance PC-766 (640 mg) as obtained in Example 2 was purified by the use of an apparatus for HPLC ("System 500" manufactured by Waters, U.S.A.) under the following operation conditions:
Column: Preppack-500/silica gel column (manufactured by Waters), two columns);
Eluting solvent: chloroform:methanol (98:2 by volume);

Flow rate: 100 ml/minute;
Detection: UV absorption at 254 nm;
Sample injection: the crude product "PC-766" (640 mg) dissolved in chloroform (30 ml) and then injected;
Fraction volume: 50 ml.

Fraction Nos. 27 and 28 were concentrated under reduced pressure to dryness to give a mixture (2 mg) of PC-766B and PC-766B'. Fraction Nos. 29 to 47 were concentrated under reduced pressure to dryness to give PC-766B (580 mg).

EXAMPLE 4

The antibiotic substance PC-766B (50 mg) as obtained in Example 3 was dissolved in methanol (100 ml) and allowed to stand at room temperature (20° to 25° C.) for methylation. After one week, the resultant solution was concentrated under reduced pressure, subjected to streak-adsorption on a preparative thin layer chromatogram and developped with a mixture of benzene and ethyl acetate (1:4 by volume). Observation was made under irradiation with UV rays. The bands of PC-766B and PC-766B' were respectively scraped off, extracted with methanol and concentrated under reduced pressure to give unreacted PC-766B (34 mg) and PC-766B' (3 mg). These products gave the physicochemical properties and biological properties as hereinabove described.

What is claimed is:

1. An antibiotic of the formula:

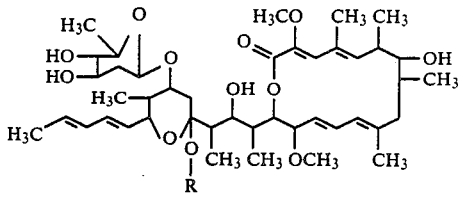

wherein R is a hydrogen atom or a methyl group.

2. The antibiotic according to claim 1, wherein R is a hydrogen atom.

3. The antibiotic according to claim 2, wherein R is a methyl group.

4. The antibiotic of claim 1 in the form of powdery crystals.

5. The antibiotic of claim 2 in the form of powdery crystals.

6. The antibiotic of claim 3 in the form of powdery crystals.

7. The compound of claim 1 in a purified form.
8. The compound of claim 2 in a purified form.
9. The compound of claim 3 in a purified form.

* * * * *